United States Patent
Segura (10) Patent No.: US 9,468,185 B2
(45) Date of Patent: Oct. 18, 2016

(54) LETTUCE PLANT

(75) Inventor: Victor Segura, Murcia (ES)

(73) Assignee: Syngenta Participations AG, Basel (CH)

( * ) Notice: Subject to any disclaimer, the term of this patent is extended or adjusted under 35 U.S.C. 154(b) by 537 days.

(21) Appl. No.: 13/993,358

(22) PCT Filed: Dec. 21, 2011

(86) PCT No.: PCT/EP2011/073593
§ 371 (c)(1),
(2), (4) Date: Jun. 12, 2013

(87) PCT Pub. No.: WO2012/085085
PCT Pub. Date: Jun. 28, 2012

(65) Prior Publication Data
US 2013/0266719 A1  Oct. 10, 2013

(51) Int. Cl.
*A01H 5/12* (2006.01)
(52) U.S. Cl.
CPC ........................................ *A01H 5/12* (2013.01)
(58) Field of Classification Search
None
See application file for complete search history.

(56) References Cited

U.S. PATENT DOCUMENTS

| | | | | |
|---|---|---|---|---|
| 6,320,104 B1 * | 11/2001 | Moor | ...................... | A01H 5/12 800/260 |
| 7,371,933 B1 | 5/2008 | Knerr | | |
| 8,772,579 B2 * | 7/2014 | Moor | ...................... | A01H 5/12 435/410 |
| 2005/0268360 A1 | 12/2005 | Gibson | | |

FOREIGN PATENT DOCUMENTS

| | | |
|---|---|---|
| EP | 1908357 | 4/2008 |
| WO | 9903329 | 1/1999 |

OTHER PUBLICATIONS

Rijk Zwaan, Innovations and Seed Services: "Lettuce and Outdoor Crops 2008", Assortment Catalogue, 2008, pp. 1-32, cited in the IDS filed Apr. 29, 2014.*
Rijk Zwaan Emerson RZ or 79-11 RZ lettuce convenience catalogue, website http://www.rijkzwaan.com/wps/wcm/connect/8ab58005-deb2-47f9-9957-208665af2351/Rijk+Zwaan_ConvenienceCatalogus+(web).pdf?MOD=AJPERES.*
Rijk Zwaan, Innovatinos and Seed Services: "Lettuce and Outdoor Crops 2008," Assortment Catalogue, p. 1-32.
International Search Report dated Mar. 16, 2012 for International Patent Application No. PCT/EP2011/073593.
International Preliminary Report on Patentability dated Jun. 13, 2013 for International Patent Application No. PCT/EP2011/073593.
Rijk Swaan, "Salanova" Retrieved from: http://www.rijkzwaan.co.uk/wps/wcm/connect/RZ+UK/Rijk+Zwaan/Products_and_Services/Products/Brands/Salanova, on Apr. 17, 2014.
Syngenta Iceberg Lettuce Icevic Product Information Sheet, Copyright 2010 Syngenta Australia Pty Ltd.

* cited by examiner

*Primary Examiner* — Eileen B O Hara
(74) *Attorney, Agent, or Firm* — Karen A. Magri (57) ABSTRACT

The present invention relates to lettuce plant that comprises leaves of substantially the same area from the inner to the outer leaves. The lettuce plant according to the invention comprises a trait that control the head formation and thus allows the lettuce not form a compact head and having leaves well separated and of substantially the same length and width. The lettuce plant can be advantageously used in the fresh cut industry for the manufacture of packaged salads.

11 Claims, 10 Drawing Sheets

FIGURE 9  Heading plant

FIGURE 10    Non Heading Plant

LETTUCE PLANT

RELATED APPLICATION INFORMATION

This application claims priority under 35 U.S.C. §371 from PCT Application No. PCT/EP2011/073593, filed Dec. 21, 2011, which claims the benefit of European Patent Application No. 10196387.4, filed Dec. 22, 2010, the disclosures of which are incorporated by reference herein in their entirety.

The present invention relates to new lettuce plants exhibiting a new head trait, to the use of such a type of new head forming lettuce plant for industrial processing as well as to the use of a new head forming lettuce for the transformation of other lettuce plants in order to get lettuce plants that differ morphologically from already existing heading lettuce plants.

Many lettuce varieties do exist nowadays on the market; more than a thousand different cultivars are available and are split into different types depending on the morphology of the plant. On the one hand, one may find the head forming type of lettuce comprising the romaine or cos type lettuce with loose upright head; the iceberg type with crispy head and the butterhead type. On the other hand the non heading lettuce group comprises mainly the oakleaf lettuce and loose leaf lettuce.

In the group of head-forming lettuce such as iceberg and romaine, because of that particular morphology, the inner leaves are small and the outer leaves are much bigger. Moreover in head-forming lettuce types, the heart of the head is to a more or lesser extent closed and cannot be reached by light. Consequently there is indeed a big heterogeneity in terms of size and colour between the inner and the outer leaves. The leaves forming the head are tightly arranged so that the inner ones are small, narrow and white or creamy while the external ones are longer, wider and greener. All together, the leaves of both iceberg and romaine lettuce are not individualized contrary to oakleaf for example and necessitate more processing.

Iceberg lettuce forms tight, dense heads that resemble cabbage surrounded by few very large external green leaves. Upon harvesting, the external bigger leaves are discarded and only the tight head is kept. The iceberg head is usually marketed as such after being wrapped into plastic foil in order to preserve it from dehydration. Iceberg lettuce is appreciated for its crispy texture and is consumed in salad, sandwiches, hamburgers and the like. Due to it compactness, the iceberg lettuces are sliced or shredded in order to get proper salad leaves parts for salad mixes or hamburgers. Indeed, due to their convex shape, iceberg leaves are not used as such in sandwiches. In order to obtain a homogeneous size of salad pieces, the cutting and shredding of external leaves needs to be repeated several time while the inner leaves do not need such an extensive cutting. Since it is not possible to control the cutting, the smaller inner leaves are damaged thereby creating browning of the edges and therefore reducing external appearance. If the cutting is limited in order to protect the smaller leaves, then the outer bigger leaves are not sufficiently cut and those bigger leaves have to be discarded or treated separately. All these processing treatments significantly increase the cost of the processed salad product obtained from iceberg lettuce.

Concerning Romaine lettuce, the problem is more or less the same since the outer leaves are long and broad as compared to the inner ones and extensive cutting is needed to obtain reasonable leaves size cuts.

Such an extensive cutting of leaves in order to achieve homogeneous size reduction induces browning of the edge of the cut leaves.

Romaine and iceberg lettuce are also appreciated by consumers because of their crispiness and freshness for home preparation of salads. However, their preparation is cumbersome since some sort of peel-off of the iceberg lettuce is necessary in order to obtain individualized leaves that need a further cutting and shredding because of the big difference in size between the outer and the inner leaves and because of their curvated shape. The romaine also necessitates separation of the leaves and cutting of the outer bigger leaves in order to get them of approximate size compared to the inner leaves which are much smaller.

There is therefore a need for lettuce type plants that address the above mentioned problems.

Accordingly, the present invention provides a lettuce plant of a given type which comprises an inheritable genetic trait causing non-heading phenotype.

The "non-heading phenotype" herein also defined as "non-heading trait" means that the lettuce plant does not form a tight head and consequently substantially all the leaves of the lettuce plants according to the present invention have substantially the same dimension in terms of length and width, ie area, from the inner leaves to the outer leaves. This means that, as compared to a normal lettuce plant of a same given type, the lettuce plant according to the present invention exhibit inner leaves that are bigger, in width and length, thus consequently they are similar in size to the external leaves. The lettuce plant according to the present invention comprises leaves that all have substantially the same area. Thus according to one embodiment, a lettuce plant according to the invention comprises leaves having substantially the same area because the leaves have substantially the same width and length.

The term "given type" of lettuce plant as it relates to a lettuce plant according to the present invention can mean a variety of lettuce plant which fulfills the necessary criteria of having distinctness, uniformity and stability in accordance with the UPOV regulations, 1991.

The term "lettuce plant" when applied to a plant according to the present invention can, in one embodiment, mean a wild lettuce plant. In one embodiment it can mean a cultivated lettuce plant. In one embodiment, the lettuce plant is *Lactuca sativa*.

The benefits of the non-heading plant according to the present invention are readily apparent to the skilled person. Accordingly, in one embodiment a lettuce plant according to the present invention has an increased yield compared with a plant without the non-heading phenotype. In one embodiment, a plant according to the present invention requires less cutting to obtain leaves of substantially the same size as a plant without the non heading phenotype. In one embodiment, a plant according to the present invention suffers reduced enzymatic browning during the cutting process.

The plant of the present invention can also have several important agronomic traits in addition to the non heading phenotype. In one embodiment, a plant according to the present invention is resistant to Downy Mildew disease. In one embodiment, a plant according to the present invention is resistant to *Nasonovia*.

According to one embodiment, a lettuce plant according to the present invention is characterized in that the non-heading phenotype corresponds to a phenotype wherein substantially all the leaves of the lettuce have substantially the same area. The area of each leaf is measured at the ready to harvest stage of growth. In one embodiment, the ready to harvest stage is 45 to 60 days after transplanting when grown under conditions typical for growing lettuce in the climate of Murcia, Spain. In one embodiment, the ready to harvest stage is 50 to 55 days after transplanting when grown under these conditions.

A plant according to the present invention has leaves of substantially the same area because the leaves of the plant have substantially the same width and substantially the same length. Many prior art plants, for example the well known Salanova, do not have leaves with the combination of substantially the same width and substantially the same length. Lettuce plants according to the present invention can thus be readily distinguished from prior art lettuce plants by the skilled person.

According to one embodiment, the lettuce plant according to the present invention is selected from the group comprising romaine type and iceberg type lettuce, preferably wherein, the lettuce plant according to the invention has all the features of a romaine or iceberg lettuce plant but has a non heading phenotype.

According to another embodiment of the present invention, the lettuce plant belongs to the iceberg type, preferably wherein, the lettuce plant according to the invention has all the features of an iceberg lettuce plant but has a non heading phenotype.

According to another embodiment of the present invention, the lettuce plant belongs to the romaine type, preferably wherein, the lettuce plant according to the invention has all the features of a romaine lettuce plant but has a non heading phenotype.

In one embodiment, the lettuce plant according to the present invention is *Lactuca sativa*. In one embodiment, a plant according to the present invention is a hybrid. In another embodiment, the lettuce plant of the invention is an inbred line.

By the expression "substantially all the leaves" of the lettuce plant means up to 75%, preferably up to 76, 77, 78, 79, 80, 81, 82, 83, 84, 85, 86, 87, 88, 89, or even up to 90% of the leaves of the lettuce plant.

The expression "same dimension" means that, on the one hand the length of substantially all the leaves of the lettuce plant are comprised substantially within the same number from the inner leaves to the outer leaves and, on the other hand that the width of substantially all the leaves of the lettuce plant is substantially the same from the inner leaves to the outer leaves.

The expression "substantially the same area" means that the area of substantially all the leaves is comprised around the same average value within a deviation of about +/−15%, particularly +/−12%, more particularly +/−10%. Concretely, as a matter of example, it means that if the average area value is 100 $cm^2$, then the area of substantially all the leaves may range from 85 to 115 $cm^2$, particularly from 88 to 112 $cm^2$, more particularly from 90 to 110 $cm^2$.

For reasons of practicality, as herein described, the area of the leaf is calculated by multiplying the width by the length of the leaf once detached from the plant. The width is measured at its higher value, meaning the widest point along the width of the leaf, and the length is measured from the top of the leaf till the basal extremity of the leaf once detached from the plant.

Due to the fact that the present invention concerns an inheritable trait conferring a non-heading phenotype wherein the leaves of the head are opening and arrange themselves in an open head instead of tightly closed head, the absolute value of the length and of the width of the leaves is not particularly relevant as such since the inheritable trait of non-heading can be introgressed in any lettuce, particularly in any iceberg or romaine lettuce. The inheritable non-heading trait does not govern the absolute length and width of the leaves of the lettuce of the present invention, but rather their distribution.

In the case of iceberg lettuce as exemplified in the examples section that correspond to usual iceberg lettuce type, because of the high number of leaves and because of the average short length, the average leaf length of substantially all the leaves is comprised in a range of from 12 to 18 cm, particularly from 13 to 17 cm, more particularly from 14 to 17 cm. Similarly the average leaf width of substantially all the leaves of iceberg lettuce type according to the invention are comprised in a range of from about 12 to 18 cm, particularly from about 13 to 17 cm, more particularly from about 14 to 17 cm. However, again, depending on the genetic background of the iceberg lettuce type in which the non-heading trait is introgressed, the width of the leaves may be different from one plant to another. The invention lies in the narrow range of the width of substantially all the leaves rather than in the absolute value of that width. The non-heading trait according to the present invention does not increase or decrease the width of the leaves but renders that width homogeneous from the inner leaves to the outer leaves.

In the case of iceberg lettuce as exemplified in the example section that correspond to usual iceberg lettuce type, because of the high number of leaves and because of the average short length of the outer leaves, the average leaf length of substantially all the leaves is comprised in a range of from about 18 to 24 cm, particularly from about 19 to 23 cm, more particularly from about 19 to 22 cm. Similarly the average leaf width of substantially all the leaves of iceberg lettuce type according to the invention is comprised in a range of from about 7 to 10 cm, particularly from about 8 to 10 cm. However, again, depending on the genetic background of the iceberg lettuce type in which the non-heading trait is introgressed, the length of the leaves may be different from one plant to another. The invention lies in the narrow range of the length of substantially all the leaves rather than in the absolute value of that length. The non-heading trait according to the present invention does not increase or decrease the length of the leaves but renders that length homogeneous from the inner leaves to the outer leaves.

All of the leaves of the lettuce plant according to the present invention have substantially the same dimensions (length and width) and so substantially all the leaves of the lettuce plant according to the present invention have an area that is substantially the same. In respect of the area of the leaves, it is in general not possible to give any value since such area is closely dependant on the genetic background in which the "non-heading" trait according to the present invention is introgressed. Indeed, among the thousands of lettuce cultivars, particularly romaine and iceberg cultivars, there is a strong variation of the surface of the leaves. The area of the leaves may be evaluated by multiplication of the leaf lengths with the leaf widths in order to get an area number or value.

In order to transfer the inheritable genetic determinant that is responsible for the non-heading trait to another plant backcross breeding can be used. For this a desirable homozygous cultivar or inbred is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent (non-heading trait, ie substantially all the leaves of the have the same dimensions) are selected and repeatedly crossed (backcrossed) to the recurrent parent. The resulting plant is expected to have the attributes of the recurrent parent (e.g., cultivar) and the desirable trait transferred from the donor parent. In case the inheritance of the red colouration is more complex than the inheritance of the other desired trait, or combination of traits, the parent with red-coloured heart leaves can be used as recurrent parent, and the parent with the other desired trait, or combination of traits, can be used as donor parent. Descriptions of other breeding methods that are commonly used for different traits and crops can be found in one of several reference books (e.g., "Principles of Plant Breeding" John Wiley and Son, pp. 115-161, 1960; Allard, 1960; Simmonds, 1979; Sneep et al., 1979; Fehr, 1987).

Suitable donor parent for the non-heading trait according to the present invention may be the lettuce plant, *Lactuca sativa* IN 9098.1, representative seeds of which have been deposited at NCIMB (Ferguson Building, Craibstone Estate, Bucksburn, Aberdeen AB219YA, Scotland) under N° NCIMB 41774 on Nov. 16, 2010.

Another suitable donor parent for the non-heading trait according to the present invention may be the lettuce plant, *Lactuca sativa* LS 9487, representative seeds of which have been deposited at NCIMB (Ferguson Building, Craibstone Estate, Bucksburn, Aberdeen AB219YA, Scotland) under N° NCIMB 41775 on Nov. 16, 2010

Lettuce plant LS 9487 is particularly suited for introgressing the non-heading trait within any Romaine lettuce background since it is genetically close to Romaine type lettuce except the fact that it contains the inheritable non-heading trait.

Lettuce plant IN 9098.1 is particularly suited for introgressing the non-heading trait with any Iceberg lettuce background since it is genetically close to Iceberg type lettuce except the fact that it contains the inheritable non-heading trait.

Plants disclosed in the present application comprise non heading trait as described herein, which non heading trait is obtainable from a lettuce plant designated IN 9098.1, representative seeds of which have been deposited at NCIMB (Ferguson Building, Craibstone Estate, Bucksburn, Aberdeen AB219YA, Scotland) under N° NCIMB 41774 on Nov. 16, 2010.

Plants disclosed in the present application comprise non heading trait as described herein, which non heading trait is obtainable from a lettuce plant designated LS9487, representative seeds of which have been deposited at NCIMB (Ferguson Building, Craibstone Estate, Bucksburn, Aberdeen AB219YA, Scotland) under N° NCIMB 41775 on Nov. 16, 2010.

Accordingly, the man skilled in the art, based on the description of the present invention and in possession of lettuce plants designated LS9487, representative seed of which is deposited under accession Number NCIMB 41775, has no difficulty transferring the non heading trait of the present invention to any other lettuce plant of various type using any breeding technique well known in the art.

The genetic information determining the non heading trait is obtainable from lettuce plant designated LS9487, representative seed of which is deposited under accession Number NCIMB 41775 or from a progeny of that plant comprising the trait.

The genetic information determining the non heading trait is obtainable from lettuce plant designated IN9098.1, representative seed of which is deposited under accession Number NCIMB 41774 or from a progeny of that plant comprising the trait.

Using the teaching as disclosed herein, the genetic information determining the trait of non heading can be transferred to another Romaine lettuce plant, for example by crossing said plant with lettuce plant designated LS9487, representative seed of which is deposited under accession Number NCIMB 41775 or from a progeny of that deposited plant comprising the non heading trait and determining the presence of the trait in the progeny of the cross.

In one embodiment, a lettuce plant of the invention is not Salanova variety. In another embodiment, a lettuce plant of the invention is not Carolus Rijk Zwaan variety. In another embodiment, a lettuce plant of the invention is not Baby Leaf variety.

Using the teaching as disclosed herein, the genetic information determining the trait of non heading can be transferred to another iceberg lettuce plant, for example by crossing said plant with lettuce plant designated IN9098.1, representative seed of which is deposited under accession Number NCIMB 41774 or from a progeny of that deposited plant comprising the non heading trait and determining the presence of the trait in the progeny of the cross.

It has also been surprisingly found by the inventor of the lettuce plant of the present application that the non heading trait is inherited in a simple manner from one generation to the next according to Mendelian genetics (see Example 5). In one embodiment the gene responsible for the non heading trait is monogenic. In another embodiment, the gene responsible for the non-heading trait is recessive. In another embodiment, the gene responsible for the non heading trait is monogenic and recessive. In one embodiment, the F2 generation of a plant according to the present invention comprises 75% plants of the heading phenotype and 25% plants of the non heading phenotype. The effect of the non heading gene on the phenotype of the progeny plants is readily apparent to the skilled person (as an illustration, see Example 5). In one embodiment, plants of the present invention with the non heading trait have leaves which are substantially convex.

Thanks to the morphological features of the lettuce plant according to the present invention having the non-heading trait, the use of this new type of lettuce plant is particularly advantageous for the freshcut salad industry particularly for the manufacture of packaged salad food products.

Accordingly, in one embodiment, the present invention concerns the use of a lettuce plant according to the present invention for the manufacture of packaged food such as salad in bag.

Due to the fact that all the leaves of the lettuce plant according to the present invention have substantially the same area, the need to cut and dispose of either the bigger of smaller leaves is very much reduced as compared to classical head forming lettuce. Consequently the yield for the manufacture of packaged salad product is increased. In one embodiment, the present invention concerns a method for increasing the yield in the manufacture of packaged salad food product by using a lettuce plant according to the present invention.

Furthermore, since the leaves of the lettuce plant according to the present invention do not need extensive cutting, those leaves are less damaged and consequently they exhibits less enzymatic browning and the shelf life is increased in case of processed packaged salad product. Thus, in one embodiment, the present invention concerns a method for increasing the shelf life of packaged salad food product by using a lettuce plant according to the present invention.

EXAMPLES

The examples described herein are illustrative of the present invention and are not intended to be limitations thereon. Different embodiments of the present invention have been described according to the present invention. Many modifications and variations may be made to the methods and plants described and illustrated herein without departing from the spirit and scope of the invention.

Example 1

Pedigree and Breeding of Iceberg Lettuce IN 9098.1

Breeding line IN9098.1 originated in 2005 with the cross *lactuca sativa* cv. Longifolia Carolus by *lactuca Sativa* cv. *capitata* Icevic, two available commercial varieties. The goal was to get a breeding line combining agronomic traits, downy mildew and *Nasonovia* resistance with possible variation affecting to the heading genes in shape and in overlapping of leaves.

F3 lines were planted in 2006 in open field to start selection for agronomic traits and 5 individuals showed unique convexity and thick iceberg leaves which leads to no heading expression.

Selection process in F4 and F5 was done in open field focusing on fixation of convexity and thick iceberg leaves in 2007 and 2008 to avoid heading expression.

The most uniform F6 was named as IN9098.1 showing uniformity through different seasons in the expression of the different traits including the non-heading trait.

15 plants of IN9098.1 were grown and harvested at the ready to harvest stage. The leaves were counted and measured for their width and length.

Figure 1:
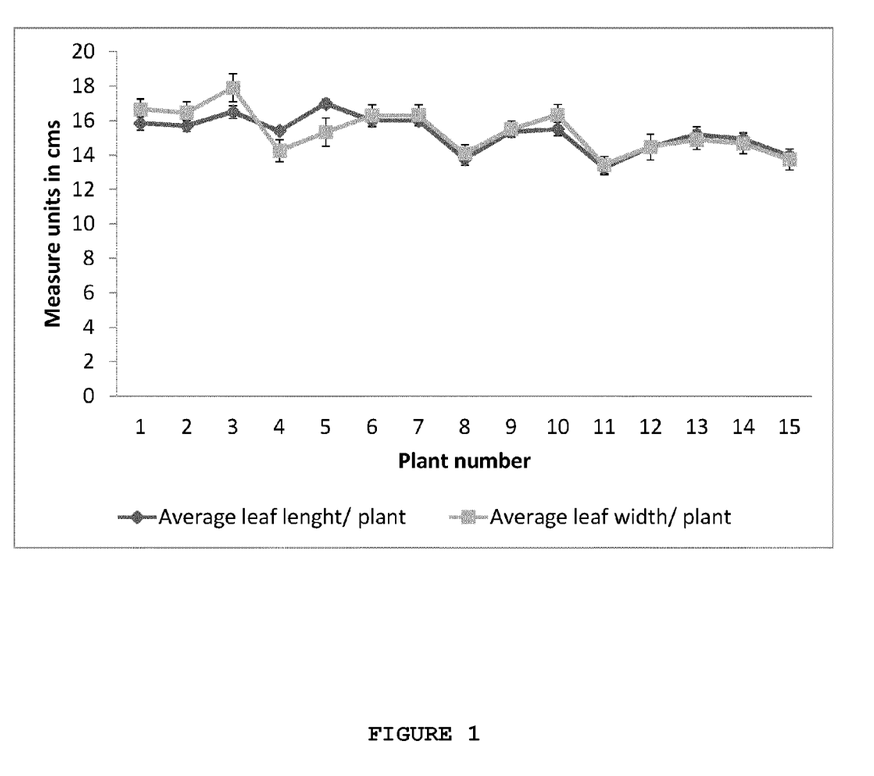
FIG. 1 shows the average leaf length and width measured on 15 lettuce heads corresponding to plants of the line IN9098.1.

FIG. 1 shows the average leaf length and width measured on 15 lettuce heads corresponding to plants of the line IN9098.1. It can be noticed that both average length and width of all the leaves of the lettuce plant remain substantially the same and thus the area of substantially all the leaves of all the 15 plants remain in the value range. The average calculated leaf area of all the leaves is about 225 cm2 (15 cm*15 cm) and, excluding the extremes, all the leaves do have substantially that area.

Example 2

Pedigree and Breeding of Romaine Lettuce LS9487

Breeding line LS9487 originated in 2004 with the cross breeding SYGNENTA line (LSA1306-74/XP4347A) 1-by *lactuca Sativa* cv. *Carolus*. The goal was to get a breeding line combining agronomic traits, downy mildew and *Nasonovia* resistance combined with the narrow and convex leaves.

F3 lines were planted in 2006 in open field to start selection for agronomic traits and 2 individuals showed unique convex and narrow leaves which led to non heading expression.

The selection process in F4 and F5 was done in open field focusing in fixation of convexity and narrow leaves during 2007 and 2008.

The most uniform F6 was named as LS9487 showing uniformity through different seasons in the expression of the different traits.

Figure 2:
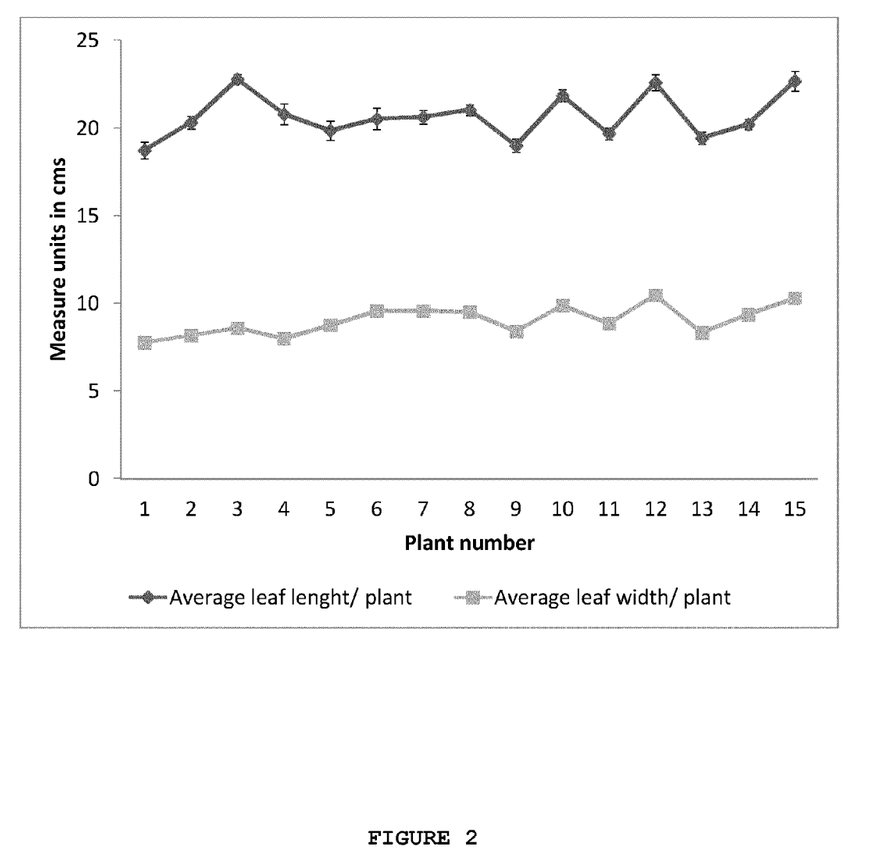
FIG. 2 shows the average leaf length and width measured on 15 lettuce heads of the plant LS9487.

FIG. 2 shows the average leaf length and width measured on 15 lettuce heads of the plant LS9487. It can be noticed that both average length and width of all the leaves of the lettuce plant remain substantially the same and thus the area of substantially all the leaves of all the 15 plant remain in the value range.

Figure 3:
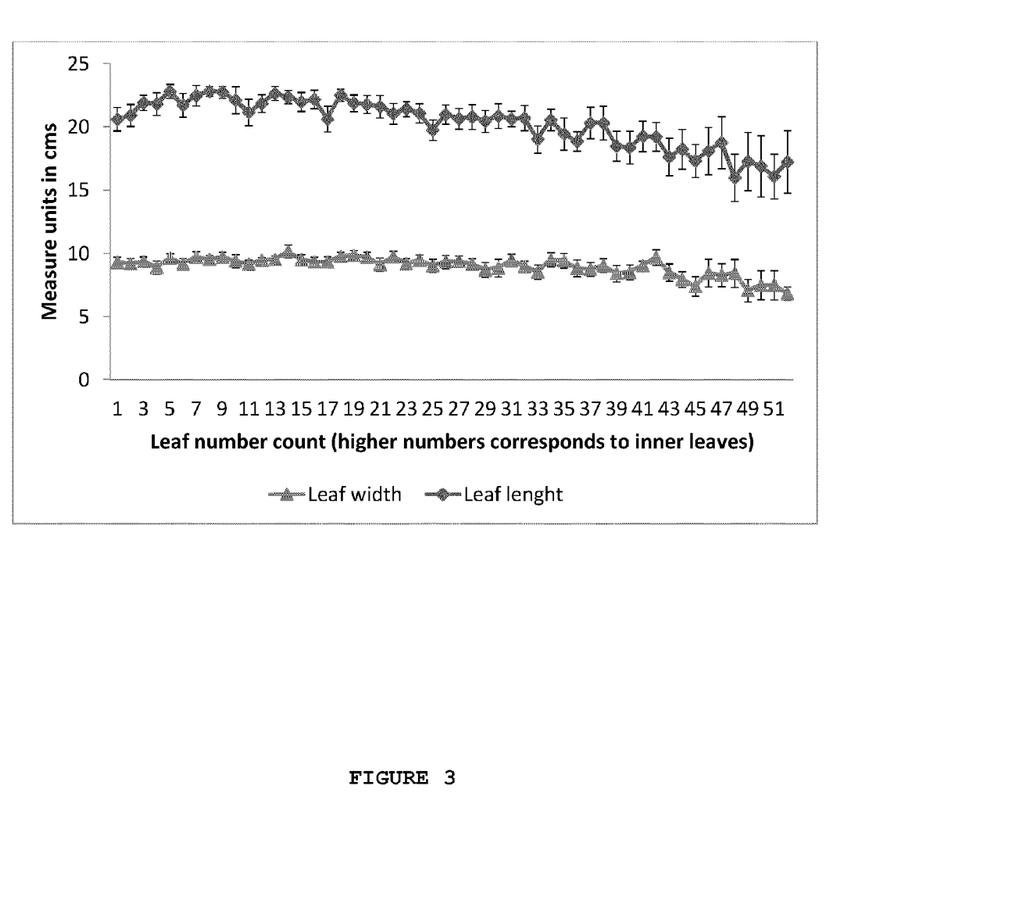
FIG. 3 shows the average length and width for each leaf measured on 15 plants from the inner leaf to the outer leaf.

FIG. 3 shows the average length and width for each leaf from the 15 plants from the inner leaf to the outer leaf. In the present case, Romaine lettuce, the total number of leaves per plant was about 50 and as seen from FIG. 3, all the leaves substantially exhibit the same length and width, or at least both dimensions do not vary in range more than 10 to 15%.

The average calculated leave area of all the leaves is about 180 cm2 (20 cm*9 cm) and, while excluding the extremes, all the leaves do have substantially that area.

Example 3

Crossing of LS9487 with a Heading Lettuce

LS9487 was crossed with a commercial Romaine lettuce, Barracuda that is a traditional Romaine lettuce with a head forming shape.

The F2 population was sown and cultivated in a traditional lettuce greenhouse.

Within that F2 population, it was possible to find 15% of the plants with the non heading trait according to the present invention thus showing that this non heading trait, is inheritable and transferable to the progeny after crossing of the deposited material with any other lettuce material that does not contain that non heading trait.

Example 4

Comparison of Expedition, IN9098, LS9487 and Salanova

Trials were conducted to compare leaf width and leaf length in several varieties. Data was collected in 2010 and 2011.

Figure 4:
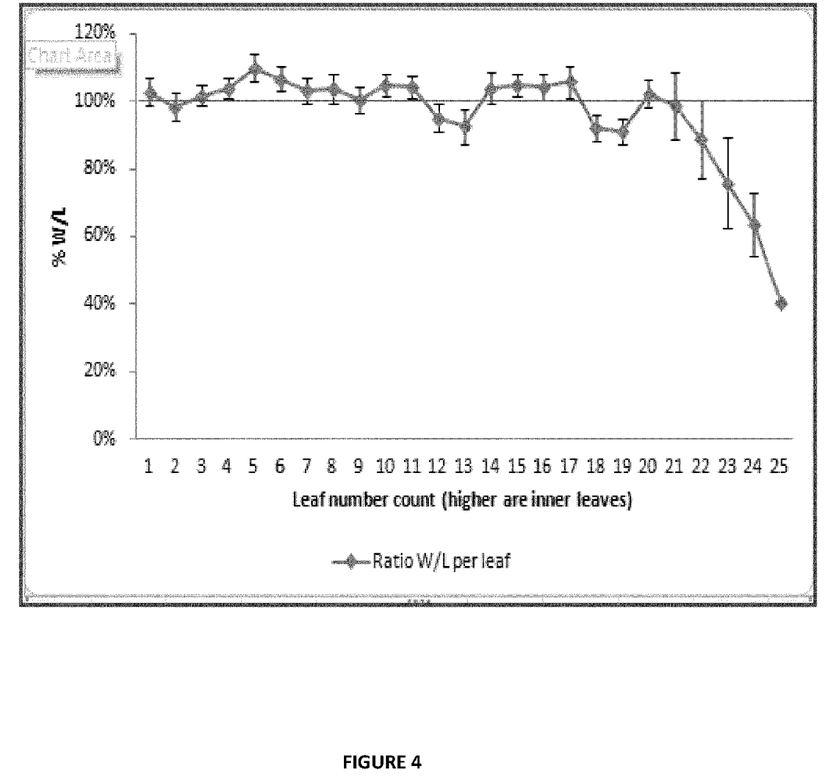
FIG. 4 shows data collected from 2010 related to the ratio of width to length per leaf for IN9098.
Figure 5:
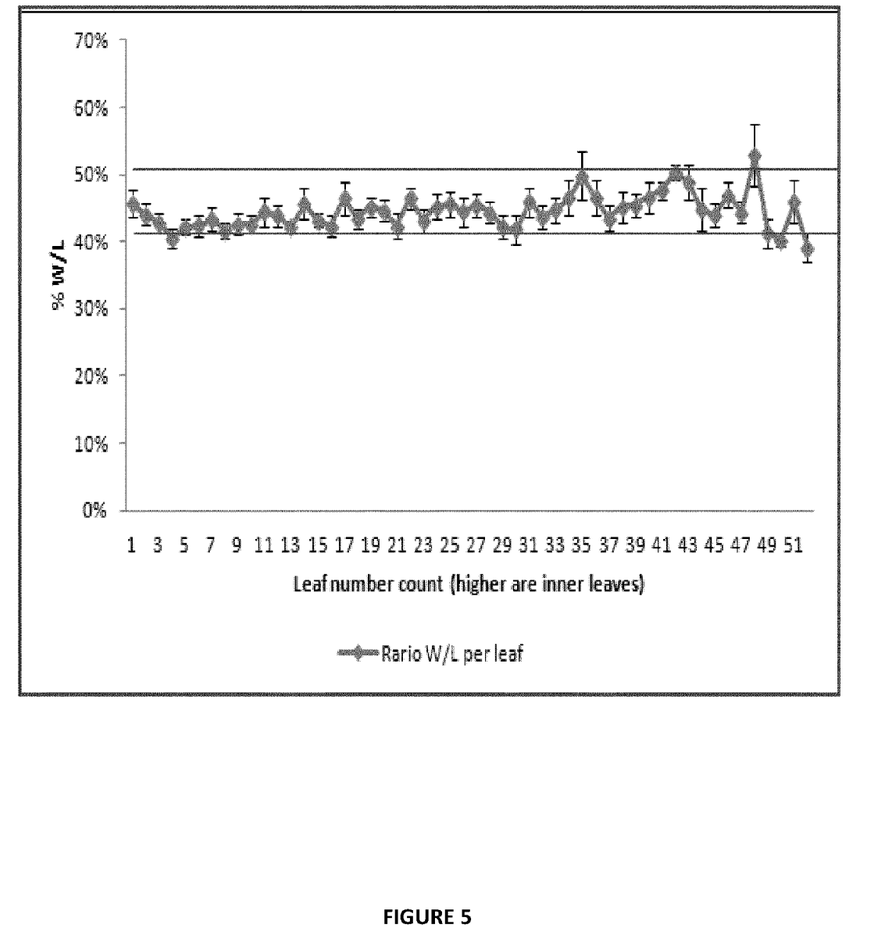
FIG. 5 shows data collected from 2010 related to the ratio of width to length per leaf for LS9487.

Data collected from 2010 related to IN9098 (FIG. 4), and LS9487 (FIG. 5).

Figure 6:
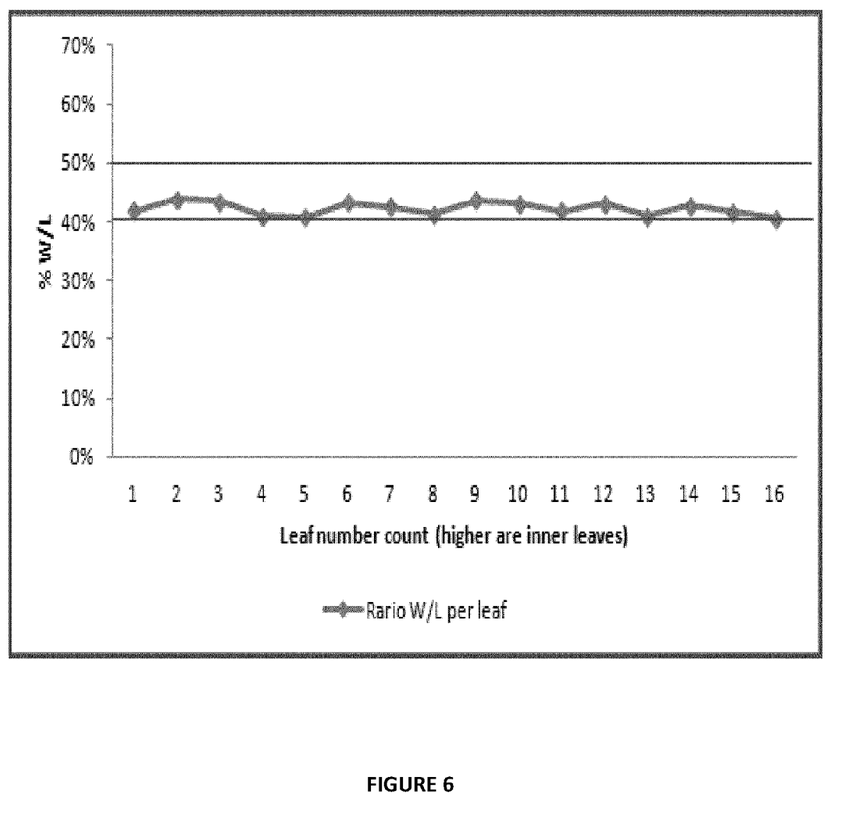
FIG. 6 shows data collected from 2011 related to the ratio of width to length per leaf for LS9487.
Figure 7:
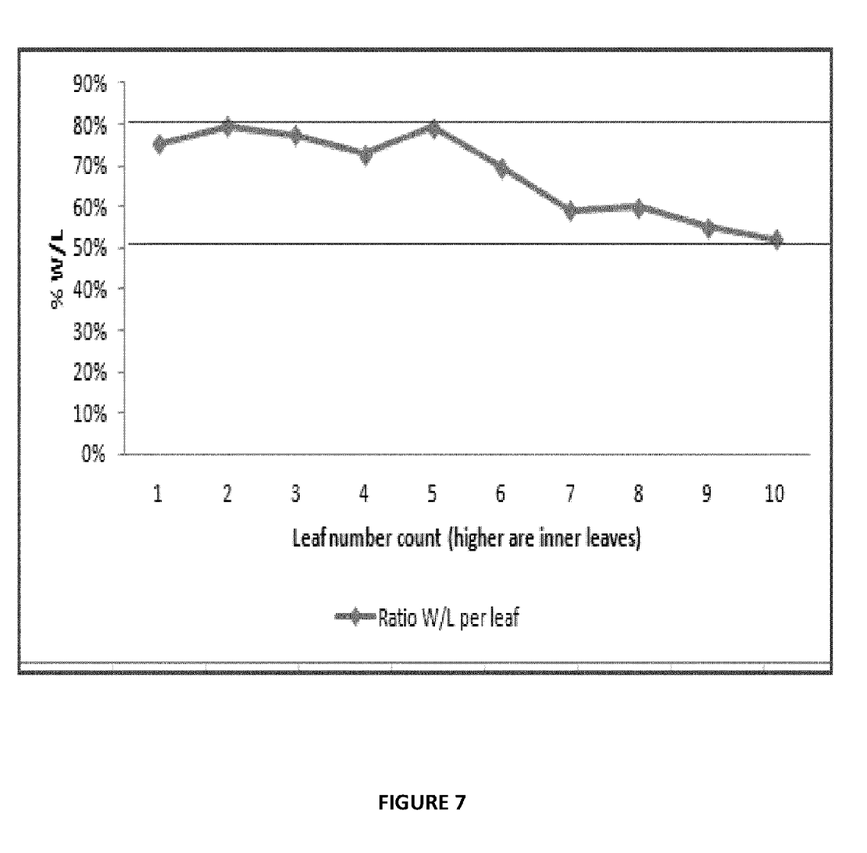
FIG. 7 shows data collected from 2011 related to the ratio of width to length per leaf for prior art Salanova type.
Figure 8:
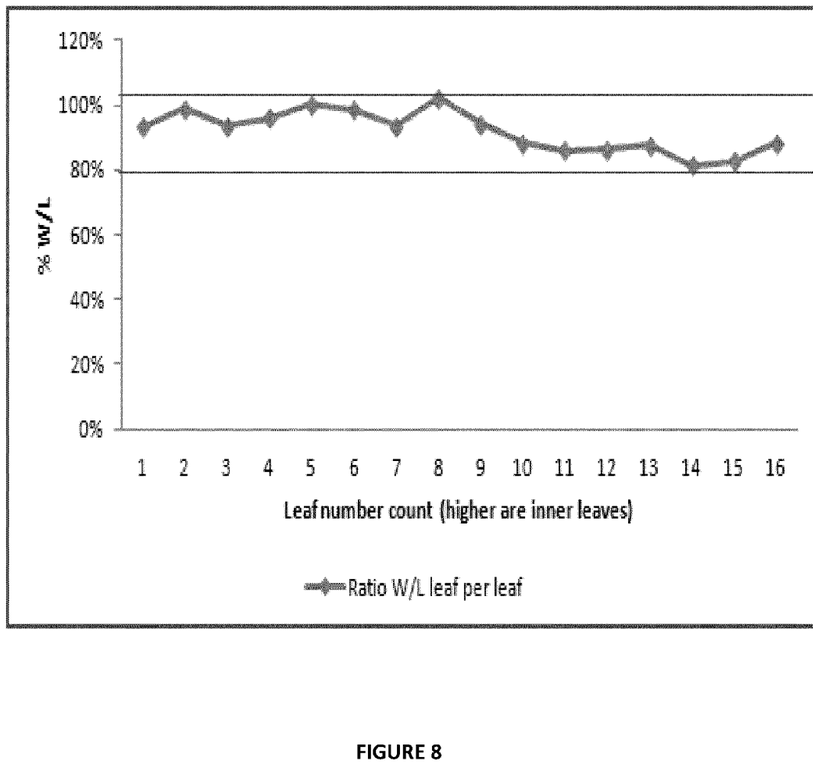
FIG. 8 shows data collected from 2011 related to the ratio of width to length per leaf for IN9098.

Data collected from 2011 show a clear variation in Expedition (inner leaves are more narrow than outer leaves; data not shown). LS9487 and IN9098 have a very narrow range of values for % W/L (see FIGS. 6 and 8 respectively). This is clearly different from prior art Salanova type (FIG. 7). In Salanova, width changes dramatically from the outer leaves to the inner leaves.

Example 5

Inheritance of the Non Heading Phenotype

Figure 9:
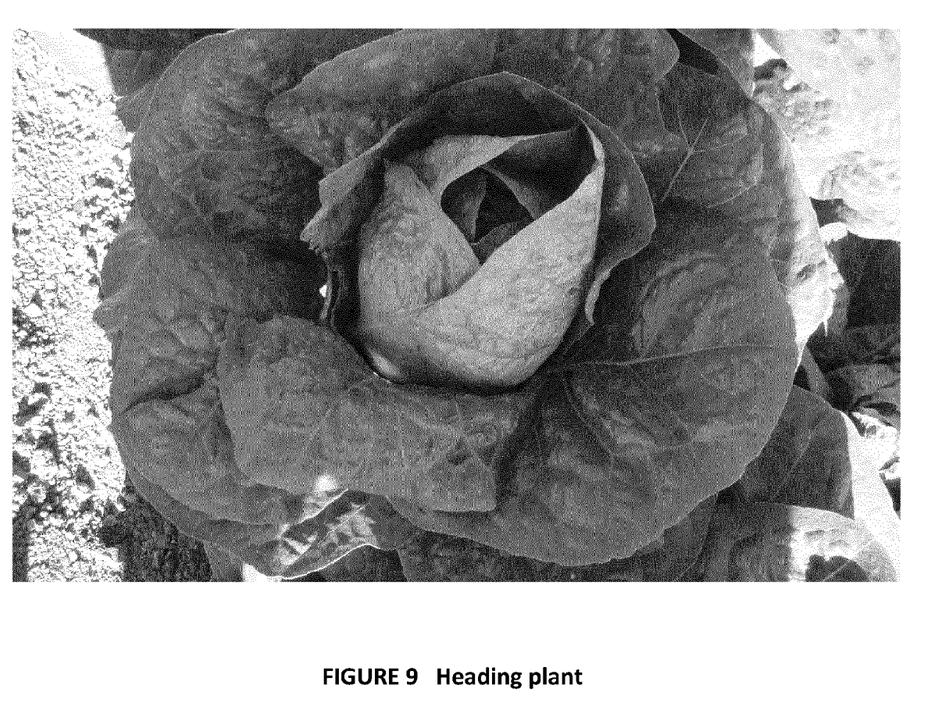
FIG. 9 shows a photograph of a heading lettuce plant.
Figure 10:
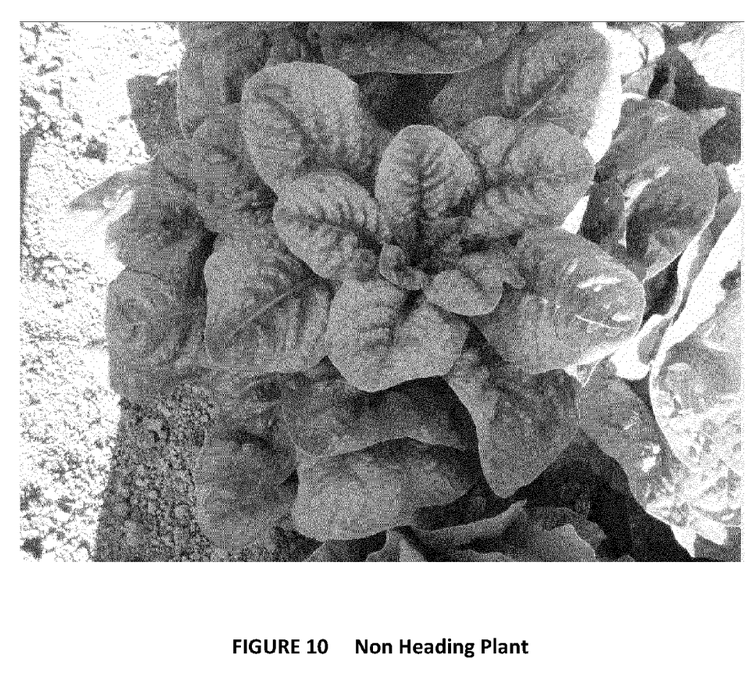
FIG. 10 shows a photograph of a non-heading lettuce plant.

In an experiment to determine the way in which the non-heading trait is inherited from one generation to the next, a cross was performed between heading type Cos Barracuda and non heading type Cos LS9487. It was surprisingly found that the F2 progeny of that cross were 75% heading and 25% non heading. Examples of both these traits can be seen in FIGS. 9 and 10 respectively. The trait can thus be described as being monogenic and recessive. In the F2 population of the current study, it seems that the recessive gene is responsible for non heading. The 25% of non heading plants containing the recessive gene in homozygosis have leaves which tend to remain convex while the other 75% of the F2 population are able to form a head. The leaves of the heading progeny turn concave at the last moment of development. This observation has not previously been described in the literature.

The invention claimed is:

1. A non-heading lettuce plant which comprises an inheritable genetic non-heading trait causing non-heading phenotype, wherein said non-heading trait is the non-heading trait of:
   (a) a lettuce plant designated IN 9098.1, representative seeds of which have been deposited at NCIMB (Ferguson Building, Craibstone Estate, Bucksburn, Aberdeen AB219YA, Scotland) under N° NCIMB 41774; or
   (b) a lettuce plant designated LS 9487, representative seeds of which have been deposited at NCIMB (Ferguson Building, Craibstone Estate, Bucksburn, Aberdeen AB219YA, Scotland) under N° NCIMB 41775.

2. A lettuce plant according to claim 1 characterized in that the non-heading phenotype corresponds to a phenotype wherein substantially all the leaves of the lettuce have substantially the same area.

3. A lettuce plant according to claim 2 characterized in that the area of substantially all the leaves are comprised around the same average value within a deviation of about +/−15%, particularly about +/−12%, more particularly about +/−10%.

4. A lettuce plant according to claim 2 wherein up to 75%, preferably up to 76, 77, 78, 79, 80, 81, 82, 83, 84, 85, 86, 87, 88, 89, or even up to 90% of the leaves have substantially the same area.

5. A lettuce plant according to claim 1 characterized in that the lettuce plant is selected from the group comprising romaine type and iceberg type lettuce.

6. A method for introducing an inheritable genetic non-heading trait into a lettuce plant, the method comprising crossing the lettuce plant of claim 1 with a second lettuce plant, wherein said second lettuce plant is a head-forming lettuce plant, to produce progeny comprising the inheritable genetic non-heading trait.

7. The method of claim 6, wherein the lettuce plant of claim 1 is LS 9487 and the second lettuce plant is a romaine lettuce plant.

8. The method of claim 6, wherein the lettuce plant of claim 1 is IN 9098.1 and the second lettuce plant is an iceberg lettuce plant.

9. A method for producing a lettuce plant comprising a non-heading phenotype, the method comprising:
   (a) crossing the lettuce plant of claim 1 with a second lettuce plant, wherein said second lettuce plant is a head-forming lettuce plant, to produce progeny;
   (b) using said progeny of (a) in a back-crossing breeding program with the lettuce plant of claim 1 as the recurrent parent for one or more generations, to produce a progeny lettuce plant comprising the non-heading phenotype.

10. The method of claim 9, wherein the lettuce plant is LS 9487 and the second lettuce plant is a romaine lettuce plant.

11. The method of claim 9, wherein the lettuce plant is IN 9098.1, and the second lettuce plant is an iceberg lettuce plant.

* * * * *